(12) United States Patent
Halleck et al.

(10) Patent No.: US 6,416,483 B1
(45) Date of Patent: Jul. 9, 2002

(54) SENSOR AND METHOD FOR DETECTING VERY LOW FREQUENCY ACOUSTIC SIGNALS

(75) Inventors: Michael E. Halleck, Longmont; Michael D. Halleck, Northglenn, both of CO (US); Michael L. Lehrman, Washington, DC (US)

(73) Assignee: iLife Systems, Inc., Dallas, TX (US)

( * ) Notice: Subject to any disclaimer, the term of this patent is extended or adjusted under 35 U.S.C. 154(b) by 0 days.

(21) Appl. No.: 09/536,104

(22) Filed: Mar. 24, 2000

(51) Int. Cl.⁷ ................................................ A61B 5/00
(52) U.S. Cl. ..................................... 600/561; 600/586
(58) Field of Search ............................... 600/486, 487, 600/488, 508, 586, 561

(56) References Cited

U.S. PATENT DOCUMENTS

| | | | |
|---|---|---|---|
| 3,858,575 A | 1/1975 | Rose | 128/2.05 S |
| 4,306,567 A | 12/1981 | Krasner | 128/671 |
| 4,494,553 A | 1/1985 | Sciarra et al. | 128/721 |
| 4,672,976 A | 6/1987 | Kroll | 128/715 |
| 4,905,706 A | 3/1990 | Duff et al. | 128/701 |
| 4,934,375 A | 6/1990 | Cole et al. | 128/673 |
| 5,086,776 A | * 2/1992 | Fowler, Jr. et al. | 600/455 |
| 5,450,854 A | 9/1995 | Kodama et al. | 128/732 |
| 5,550,902 A | 8/1996 | Abbruscato | 379/106 |
| 5,564,494 A | 10/1996 | Halperin et al. | 128/748 |
| 5,605,156 A | 2/1997 | Drzewiecki et al. | 128/672 |
| 5,825,895 A | 10/1998 | Grasfield et al. | 381/67 |
| 6,048,319 A | 4/2000 | Hudgins et al. | 600/528 |
| 6,099,486 A | 8/2000 | Fruscello | 600/586 |
| 6,213,955 B1 | 4/2001 | Karakasoglu et al. | 600/529 |
| 6,261,237 B1 | 7/2001 | Swanson et al. | 600/527 |

* cited by examiner

*Primary Examiner*—Kevin Shaver
*Assistant Examiner*—Pamela Wingood

(57) ABSTRACT

There is disclosed a sensor and method for detecting very low frequency acoustic signals. The sensor is capable of detecting low frequency acoustic signals in the frequency range of one tenth Hertz to thirty Hertz. The sensor comprises a chamber having portions that form a cavity and a low frequency microphone placed within the cavity. An alternate embodiment of the invention comprises a chamber having portions that form a resonant cavity, a low frequency microphone placed within the resonant cavity, and a membrane that covers the resonant cavity. Low frequency acoustic signals that are incident on the membrane cause the membrane to move and amplify the acoustic signals within the resonant cavity.

19 Claims, 3 Drawing Sheets

SENSOR AND METHOD FOR DETECTING VERY LOW FREQUENCY ACOUSTIC SIGNALS

RELATED APPLICATIONS

A related patent application by M. E. Halleck and M. D. Halleck has been filed concurrently with this patent application entitled "Apparatus and Method for Detecting Very Low Frequency Acoustic Signals" (Attorney Docket No. ILIF01-00036). A related patent application by M. E. Halleck, M. D. Halleck, M. L. Lehrman and A. R. Owen has been filed concurrently with this patent application entitled "Physiological Condition Monitors Utilizing Very Low Frequency Acoustic Signals" (Attorney Docket No. ILIF01-00053). A related patent application by M. E. Halleck and M. D. Halleck has been filed concurrently with this patent application entitled "System and Method for Remotely Monitoring At Least One Physiological Characteristic of a Child" (Attorney Docket No. 34). Another related patent application by M. E. Halleck, M. D. Halleck and G. V. Halleck has been filed concurrently with this patent application entitled "System and Method for Seizing a Communication Channel in a Commercially Available Child Monitor" (Attorney Docket No. ILIF01-00054).

TECHNICAL FIELD OF THE INVENTION

The present invention is directed to a sensor and a method for detecting very low frequency acoustic signals. The sensor of the present invention comprises a chamber and a microphone for detecting very low frequency acoustic signals in the frequency range of one tenth Hertz (0.1 Hz) to thirty Hertz (30.0 Hz).

BACKGROUND OF THE INVENTION

Microphones in physiological condition monitors are used to detect sounds that are indicative of physiological processes. Physiological condition monitors are capable of obtaining and recording signals indicative of a person's physiological processes. The most commonly monitored physiological processes are respiration and cardiac activity. Physiological condition monitors that monitor respiration and cardiac activity usually comprise one or more sensors coupled to the body of the person whose physiological conditions are to be measured. The sensors are capable of sensing changes in physical parameters that are caused by the person's respiration and cardiac activity. Physiological condition monitors measure and record waveform signals received from the sensors. Electrocardiogram (ECG) waveform signals are the most commonly used waveforms for measuring a person's cardiac activity. Respiration waveform signals may be electronically derived using techniques such as impedance pneumography or inductive plethysmography. Respiration waveform signals are used to measure a person's breathing rate and other types of information concerning respiration.

The present invention comprises a chamber and a microphone that is capable of detecting very low frequency acoustic signals. The present invention is particularly useful in that it may be used to detect and monitor physiological conditions. For purposes of illustration, the present invention will be described with reference to physiological condition monitors that are capable of monitoring respiration and cardiac activity. It is understood however, that the present invention is not limited to use in respiration monitors, and is not limited to use in cardiac activity monitors, and is not limited to use in physiological condition monitors in general. The present invention may be used to detect any type of very low frequency acoustic signal.

Low heart rate is referred to as bradycardia. High heart rate is referred to as tachycardia. Cessation of respiration is referred to as apnea. When a person exhibits apnea, bradycardia or tachycardia a life threatening condition very likely exists. Physiological condition monitors that are capable of continuously monitoring a person's respiration and cardiac activity are extremely useful for quickly detecting apnea, bradycardia or tachycardia. Such physiological condition monitors are also useful for quickly detecting other abnormal conditions such as a very slow breathing rate or a very high breathing rate.

Infants who are susceptible to sudden infant death syndrome are known to exhibit apnea and bradycardia. Physiological condition monitors that are capable of continually monitoring respiration and cardiac activity are particularly useful in the early detection of apnea or bradycardia in infants. Most physiological condition monitors are equipped with an alarm system to sound an alert when such conditions are detected.

A physiological condition monitor may be coupled directly to a person who is a patient in a hospital bed. In such an arrangement the waveform signals from the sensors coupled to the patient's body may be sent through wires directly to a detector circuit (and other circuitry) located in a console by the patient's bed. The wires attached to the patient restrict the patient's movements and frequently become tangled as the patient moves. The tangling of the wires can also result in the sensors becoming detached from the patient. The loss of sensor contact can set off an alarm signal.

In other cases it is more practical to provide one or more sensors located in a belt, harness or item of clothing that is to be worn by the person to be monitored. In this type of physiological condition monitor the waveform signal information from the sensors is transmitted via a radio frequency transmitter to a radio frequency receiver in a base station unit that is located away from the site of the physiological condition sensors. The base station unit contains circuitry for analyzing and recording the waveform signal information. The base station unit contains circuitry for detecting abnormal conditions in the person's breathing (such as apnea) or abnormal conditions in the person's cardiac activity (such as bradycardia or tachycardia). Because of the freedom of movement that this type of monitor provides, it is the preferred type of monitor for monitoring the physiological conditions of infants.

If the data that is acquired by the physiological condition monitor is not transmitted to the base station unit and recorded there, then the data may be recorded in a memory data storage device located within the physiological condition monitor. To preserve the freedom of movement that is provided by a monitor that is worn on a belt, harness or item of clothing, the memory data storage device within the physiological condition monitor must be battery powered.

Electrocardiogram (ECG) waveform signals are commonly used to obtain information concerning a person's cardiac activity. To obtain ECG waveforms an ECG sensor unit is coupled to the person whose cardiac activity is to be measured. The ECG sensor unit is coupled to the person via electrodes capable of receiving signals that are representative of cardiac activity directly from the person's body. In such an arrangement the electrodes must be attached directly to the person's skin in order to receive the signals. The ECG sensor unit receives the ECG electrical signals from the electrodes. The ECG signals received by the ECG sensor unit are then either recorded within the physiological condition monitor or transmitted to a base station unit.

It is possible to obtain information about cardiac activity from acoustic signals. For example, U.S. Pat. No. 4,306,567 to Krasner discloses a sensor apparatus coupled directly to the skin of a person. The Krasner sensor apparatus is capable of detecting acoustic signals from cardiac contractions within a frequency bandwidth between about thirty Hertz (30.0 Hz) and ninety Hertz (90.0 Hz). The acoustical energy associated with the cardiac contractions detected by the Krasner sensor apparatus exhibits a maximum signal-to-noise ratio at about forty five Hertz (45.0 Hz).

The Krasner sensor apparatus is also capable of detecting acoustic signals from breathing activity (i.e., respiration) within a frequency bandwidth between about three hundred Hertz (300.0 Hz) and six hundred Hertz (600.0 Hz). The acoustical energy associated with the breathing activity detected by the Krasner sensor exhibits a maximum signal-to-noise ratio at about four hundred Hertz (400.0 Hz). The Krasner sensor simultaneously detects both the a cardiac activity signals at about forty five Hertz (45.0 Hz) and the breathing activity signals at about four hundred Hertz (400.0 Hz) with a single sensor unit coupled directly to the skin.

Acoustic signals normally contain noise artifacts. We have determined that most of the noise artifacts present in acoustic signals due to respiration and cardiac activity may be eliminated by considering only the very low frequency components of acoustic signals. In particular, almost all noise artifacts that are present in acoustic signals that are due to respiration and cardiac activity may be totally eliminated by filtering out all components of the signal that are outside the frequency range of one tenth Hertz (0.1 Hz) to thirty Hertz (30.0 Hz). This is due to the fact most noise artifacts occur at frequencies that are higher than these frequencies.

We have also determined that sensor devices that are capable of detecting acoustic signals in the very low frequency range of one tenth Hertz (0.1 Hz) to thirty Hertz (30.0 Hz) do not need to be coupled directly to the skin of the person whose physiological conditions are being monitored. A sensor device that detects acoustic signals in the very low frequency range of one tenth Hertz (0.1 Hz) to thirty Hertz (30.0 Hz) in accordance with the principles of the present invention is capable of detecting indirect acoustic signals from the body of the monitored person through the monitored person's clothes.

For these reasons it is advantageous to be able to detect very low frequency acoustic signals in the range of one tenth Hertz (0.1 Hz) to thirty Hertz (30.0 Hz). It is also advantageous to have an apparatus for monitoring physiological conditions in which it is not necessary to couple a sensor unit directly to the skin of the person to be monitored. It is also advantageous to have an apparatus for monitoring physiological conditions that is capable of detecting acoustic signals through the monitored person's clothes.

SUMMARY OF THE INVENTION

The present invention comprises an improved apparatus and method for detecting very low frequency acoustic signals in the range of one tenth Hertz (0.1 Hz) to thirty Hertz (30.0 Hz). The very low frequency acoustic signals are useful in monitoring physiological conditions such as respiration and cardiac activity. The present invention is capable of detecting signals in a frequency range that is lower than the range of frequencies previously used to detect acoustic signals for monitoring physiological conditions.

An advantageous embodiment of the present invention comprises a chamber and a microphone that is capable of detecting very low frequency acoustic signals in the range of one tenth Hertz (0.1 Hz) to thirty Hertz (30.0 Hz) An advantageous embodiment of the chamber of the present invention comprises a closed chamber containing a fluid. The fluid may be either a liquid or a gas. In most instances the fluid that is used is air. The walls of the chamber are not completely rigid. The walls of the chamber are capable of expanding and contracting (i.e., moving inwardly and outwardly with respect to the interior cavity of the chamber) in response to external inputs of mechanical energy that form waves of very low frequency acoustical energy within the chamber.

The mechanical energy from outside the chamber forms waves of very low frequency acoustical energy within the chamber and causes the walls of the chamber to expand and contract by extremely small amounts. The extremely small expansions and contractions of the walls of the chamber cause the molecules of fluid in the chamber (usually molecules of air) to move in low frequency acoustic waves throughout the cavity of the, chamber.

The present invention further comprises a microphone within the chamber. The microphone is capable of detecting the low frequency acoustic waves of the molecules of fluid in the chamber that are caused by the mechanical energy that causes the walls of the chamber to expand and contract.

Prior art acoustic sensors directly detect higher frequency sounds that are made by the lungs during respiration or by the heart during cardiac activity. The sensor of the present invention, however, obtains information by detecting the very low frequency signals caused by the motion of the chest during respiration or cardiac activity. Almost all of the noise components in an acoustic signal have frequencies that are above the very low frequency range. By using the method of the present invention to exclude the higher frequencies of sound (and noise), the sensor of the present invention eliminates almost all the noise artifacts from the acoustic 'signal.

The present invention is capable of detecting acoustic signals from cardiac activity within a frequency bandwidth between about ten Hertz (10.0 Hz) and thirty Hertz (30.0 Hz). The acoustical energy associated with the cardiac activity detected by the present invention exhibits a maximum signal-to-noise ratio at about sixteen Hertz (16.0 Hz)

The present invention is capable of detecting acoustic signals respiration within a frequency bandwidth between about one tenth Hertz (0.1 Hz) and two Hertz (2.0 Hz). The acoustical energy associated with the respiration detected by the present invention exhibits a maximum signal-to-noise ratio at about one and one half Hertz (1.5 Hz).

It is a primary object of the present invention to provide an improved sensor and method for detecting very low frequency acoustic signals in the range of one tenth Hertz (0.1 Hz) to thirty Hertz (30.0 Hz).

It is also an object of the present invention to provide an improved sensor and method for a physiological condition monitor capable of detecting very low frequency acoustic signals in the frequency range of one tenth Hertz (0.1 Hz) to thirty, Hertz (30.0 Hz) that are indicative of physiological conditions.

It is also an object of the present invention to provide an improved sensor and method for a physiological condition monitor capable of detecting very low frequency acoustic signals indicative of physiological conditions where the sensor is not coupled directly to the skin of the person being monitored.

It is also an object of the present invention to provide an improved sensor and method for a physiological condition monitor capable of detecting very low frequency acoustic signals that are indicative of physiological conditions where the sensor is capable of detecting such signals through the clothes of the person being monitored.

It is also an object of the present invention to provide an improved sensor and method for a physiological condition monitor capable of detecting acoustic signals from cardiac activity within frequency bandwidth between about ten Hertz (10.0 Hz) and thirty Hertz (30.0 Hz).

It is a further object of the present invention to provide an improved sensor and method for a physiological condition monitor capable of detecting acoustic signals from respiration within a frequency bandwidth between about one tenth Hertz (0.1 Hz) and two Hertz (2.0 Hz).

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description, it may be advantageous to set forth definitions of certain words and phrases used throughout this patent document: the terms "include" and "comprise" and derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware, or software, or some combination of at least two of the same. It should be noted that the functionality associated with any particular controller may be centralized or distributed, whether locally or remotely. Definitions for certain words and phrases are provided throughout this patent document. Those of ordinary skill in the art should understand that in many, if not most, instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION

Figure 1:
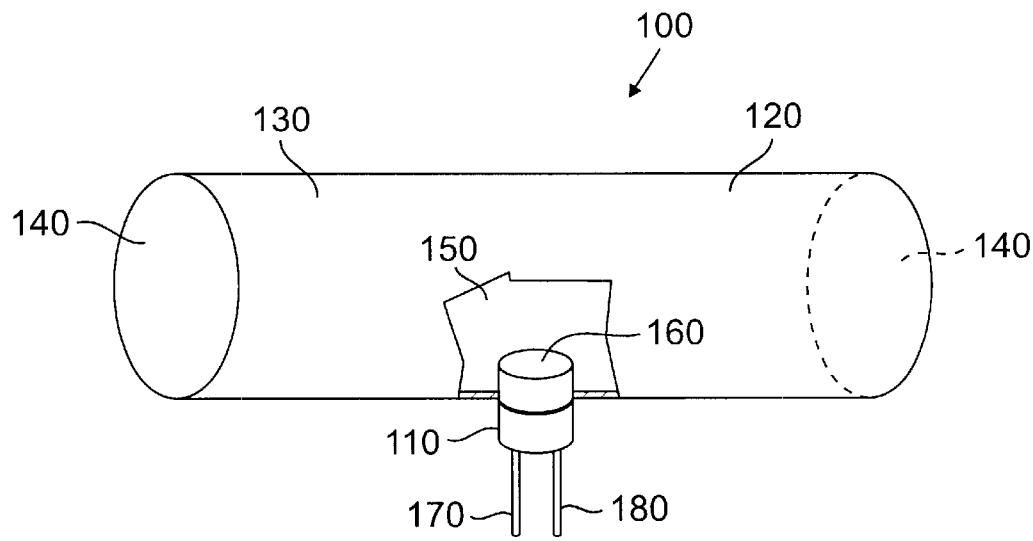
FIG. 1 is a partially cutaway view showing one embodiment of the sensor of the present invention and showing the sensor chamber as a tube and showing the placement of the microphone of the present invention in one of the side walls of the sensor chamber.
Figure 5:
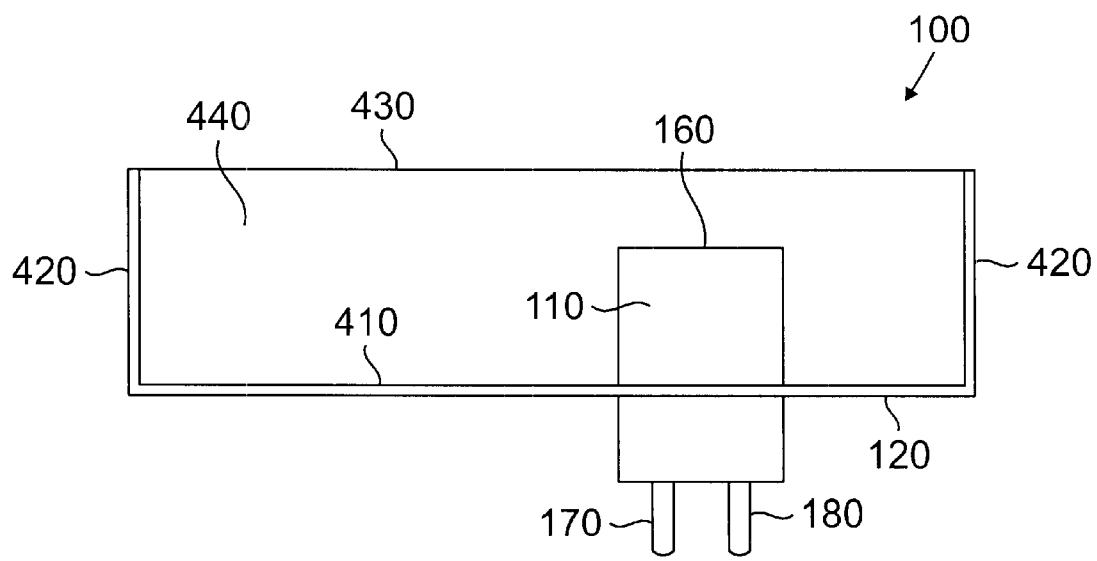
FIG. 5 is a cross sectional view of the embodiment of the microphone of the present invention shown in FIG. 4 taken along line 5—5 of FIG. 4.

FIGS. 1 and 5, discussed below, and the various embodiments used to describe the principles of the present invention in this patent document are by way of illustration only and should not be construed in any way to limit the scope of the invention. Those skilled in the art will understand that the principles of the present invention may be implemented in a suitably modified sensor.

FIG. 1 is a partially cutaway view showing an advantageous embodiment of sensor 100 of the present invention. Sensor 100 comprises a chamber 120 and a microphone 110. In this embodiment chamber 120 comprises a hollow tube having side walls 130 and end walls 140 that form cavity 150 within chamber 120. Cavity 150 of chamber 120 is filled with a fluid (not shown). The connections between side walls 130 and end walls 140 are sealed to prevent the escape of the fluid from cavity 150. The fluid may be either a liquid or a gas. In most instances the fluid that is used is air.

When the fluid that is used is air, the connections between side walls 130 and end walls 140 are not hermetically sealed. A small amount of air may pass through the connections between side walls 130 and end walls 140 to adjust for variations in ambient air pressure in the atmosphere.

Figure 2:
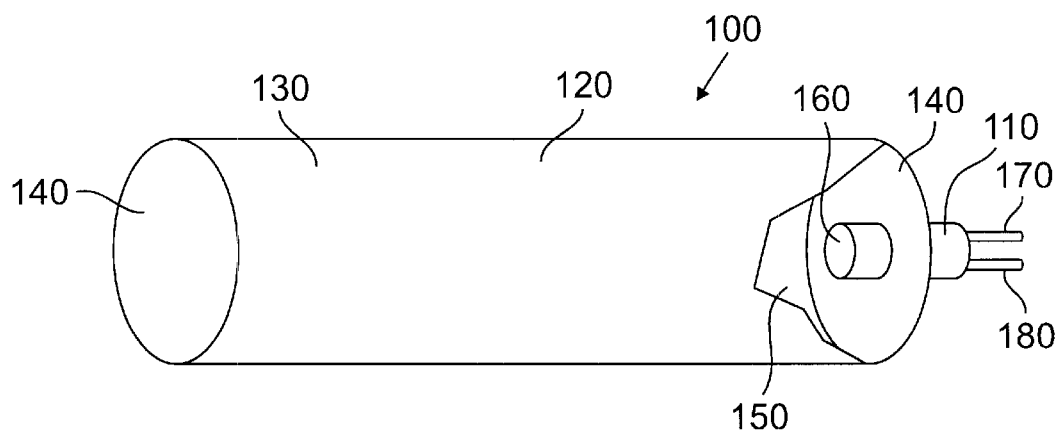
FIG. 2 is a partially cutaway view showing another embodiment of the sensor of the present invention and showing the sensor chamber as a tube and showing the placement of the microphone of the present invention in one of the end walls of the sensor chamber.

Microphone 110 is mounted within chamber 120 so that the face 160 of microphone 110 is within the fluid in cavity 150 of chamber 120. Microphone 110 may be mounted at any position within chamber 120. In one advantageous embodiment of the present invention shown in FIG. 1 microphone 110 is mounted within one of the side walls 130 of chamber 120. In an alternate advantageous embodiment of the present invention shown in. FIG. 2 microphone 110 is mounted within one of the end walls 140 of chamber 120. Microphone 110 also has microphone output cables, 170 and 180, for coupling microphone 110 to other electronic equipment (not shown in FIG. 1 or FIG. 2).

The side walls 130 (and end walls 140) of chamber 120 are constructed of material that is not completely rigid. The material used to construct the walls, 130 and 140, may be thin metal or plastic. Because the walls, 130 and 140, are not completely rigid, they are capable of expanding and contracting (i.e., moving inwardly and outwardly) with respect to the interior of cavity 150 of chamber 120. The ability of the walls, 130 and 140, of sensor 100 to expand and contract in response to the presence of waves of low frequency acoustical energy in chamber 120 is a key feature of the present invention.

When acoustical energy from a source (not shown) reaches chamber 120 of sensor 100 the acoustical energy contains both high frequency acoustic signal components and low frequency acoustic signal components. The side walls 130 and the end walls 140 of chamber 120 of sensor 100 expand and contract in response to the presence of the very low frequency acoustic signal components. The presence of waves of very low frequency acoustic energy in chamber 120 of sensor 100 cause the walls, 130 and 140, of chamber 120 to expand and contract by extremely small amounts.

The extremely small expansions and contractions of the walls, 130 and 140, of chamber 120 of sensor 100 in response to the presence of very low frequency acoustic signals cause the molecules of fluid in chamber 120 (usually molecules of air) to move in low frequency waves throughout the cavity 150 of chamber 120. Microphone 110 is capable of detecting the low frequency waves of molecules of fluid in chamber 120 that are caused by the low frequency acoustic signal components in the acoustical energy that cause the walls, 130 and 140, of chamber 120 to expand and contract.

When microphone 110 receives low frequency acoustic signals then microphone 110 generates electronic signals indicative of the intensity of the low frequency acoustic signals. Electronic processing circuits (not shown) in a physiological condition monitor (not shown) are coupled to microphone 110 through microphone output cables, 170 and 180, to receive and analyze the electronic signals that are indicative of the intensity of the low frequency acoustic signals.

The electronic processing circuits comprise electronic filters for filtering out all components of the signal that are outside the frequency range of one tenth Hertz (0.1 Hz) to thirty Hertz (30.0 Hz) . The electronic processing circuits also comprise electronic filters for filtering out all components of the signal that are outside the frequency range of one tenth Hertz (0.1 Hz) to two Hertz (2.0 Hz) to obtain a signal indicative of respiration. The electronic processing circuits also comprise electronic filters for filtering out all components of the signal that are outside the frequency range of ten Hertz (10.0 Hz) to thirty Hertz (30.0 Hz) to obtain a signal indicative of cardiac activity.

Prior art sensors directly detect higher frequency sounds that are made by the lungs during respiration or by the heart during cardiac activity. Sensor 100 of the present invention, however, obtains information by detecting the very low frequency signals caused by the motion of the chest during respiration or cardiac activity. Almost all of the noise components in an acoustic signal have frequencies that are above the very low frequency range. Using the method of the present invention to exclude the higher frequencies of sound (and noise), sensor 100 of the present invention eliminates almost all the noise artifacts from the acoustic signal.

Figure 3:
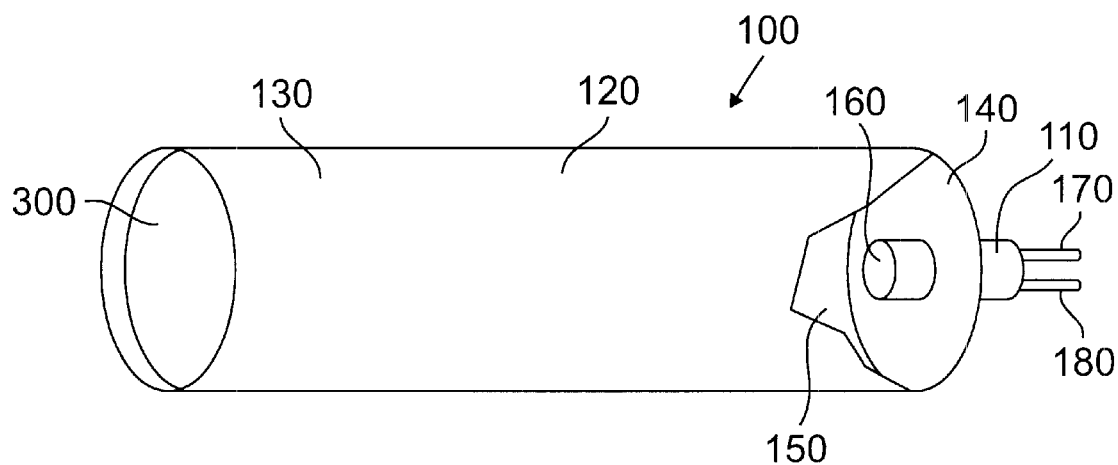
FIG. 3 is a partially cutaway view showing another embodiment of the sensor of the present invention and showing the sensor chamber as a tube with one open end and showing the placement of the microphone of the present invention in the closed end of the sensor chamber.

An alternate advantageous embodiment of the present invention is shown in FIG. 3. The embodiment shown in FIG. 3 is similar to that shown in FIG. 2 except that chamber 120 of sensor 100 comprises an open ended tube having portions that form an aperture 300. In this embodiment cavity 150 of chamber 120 has access to the surrounding atmosphere through aperture 300 in the open end of the tube. In the embodiment shown in FIG. 3 microphone 110 is placed within the end wall 140 of the closed end of the tube. Alternatively, microphone 110 could be placed within a side wall 130 of an open ended tube. This embodiment shows that it is possible to practice the invention where the fluid in chamber 120 is air that has access to the air of the surrounding environment.

Although chamber 120 of sensor 100 has been shown in the shape and form of a tube, it is clear that the invention may be practiced with a chamber 120 of sensor 100 that has a different type of shape and form. One such alternate embodiment of the present invention is shown in FIG. 4.

Figure 4:
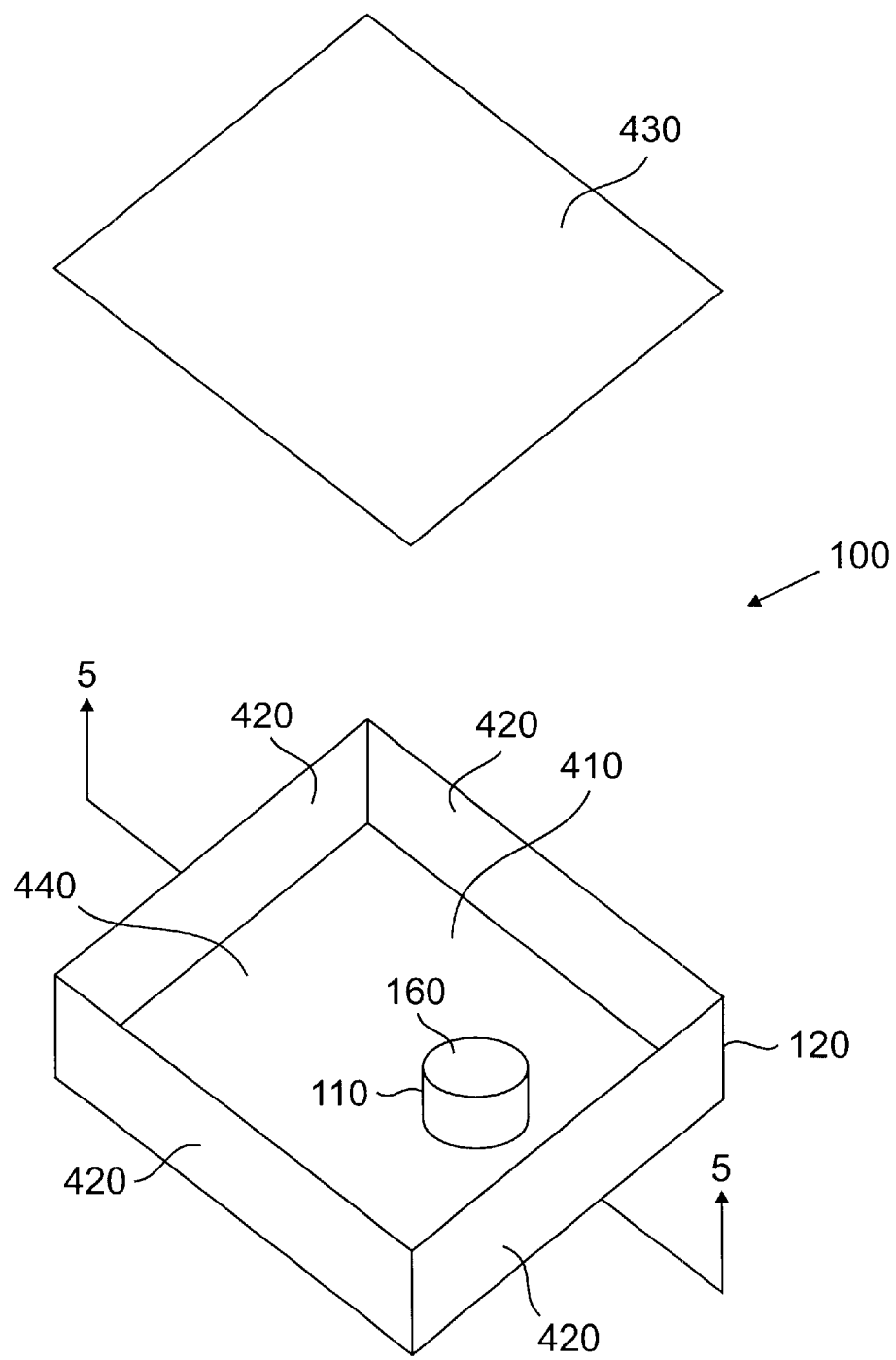
FIG. 4 is an exploded view showing another embodiment of the sensor of the present invention and showing the sensor chamber as a rectangular box and showing the placement of the microphone of the present invention within the rectangular box.

FIG. 4 shows an exploded view of an alternate advantageous embodiment of sensor 100 of the present invention. Sensor 100 comprises microphone 110 mounted within chamber 120. Microphone 110 may be mounted at any position on the interior surface of the bottom 410 of chamber 120. In the embodiment of the invention shown in FIG. 4 the shape of chamber 120 is rectangular. However, the shape of chamber 120 may be circular, elliptical, or of irregular shape. The height of the walls 420 of chamber 120 are greater than the height of microphone 110 so that microphone 110 is contained within chamber 120.

Membrane 430 covers the top of chamber 120. Membrane 430 has a shape that matches the shape of the top of chamber 120. In the embodiment of sensor 100 shown in FIG. 4, that shape is rectangular. When membrane 430 is attached to the top edges of the walls 420 of chamber 120, then a cavity 440 is formed between membrane 430 and walls 420 and bottom 410 of chamber 120. In one advantageous embodiment of the present invention, the height of the walls 420 are only slightly greater than the height of microphone 110 so that the top of microphone 110 is positioned near membrane 430.

In one advantageous embodiment of the present invention membrane 430 is made of urethane. However, membrane 430 may also be made of other suitable materials. Before membrane 430 is attached to the top of chamber 120 membrane 430 is slightly stretched. The slight stretching of membrane 430 is to make membrane 430 taut across the top of chamber 120.

When sensor 100 is used to detect acoustic signals indicative of physiological conditions, chamber 120 is placed next to the body (not shown) of the person whose physiological conditions are being monitored. Chamber 120 is placed with the outer surface of membrane 430 adjacent to a selected area of the body. It is not necessary that membrane 430 touch the skin of the body. There may be a layer of clothing between the skin of the body and membrane 430. Membrane 430 is thereby acoustically coupled to the area of the body where membrane 430 is placed.

Membrane 430 acquires very low frequency acoustic signals in the form of vibrations from the area of the body to which it is acoustically coupled. That is, as the very low frequency acoustic vibrations from the body impinge upon membrane 430 they cause membrane 430 to vibrate. These vibrations of membrane 430 cause the very low frequency acoustic vibrations to pass into cavity 440 of chamber 120. The very low frequency acoustic vibrations resonate within the enclosed space of cavity 440. FIG. 5 shows a cross sectional view of sensor 100 showing cavity 440 and one possible location for the placement of microphone 110 within cavity 440. Microphone 110 detects the very low frequency acoustic vibrations that are resonating within cavity 440.

The interaction of membrane 430 and resonant cavity 440 increases the amplitude of the very low frequency acoustic signals from the body so that microphone 110 may more easily detect the signals. The interaction of membrane 430 and resonant cavity 440 accomplishes this increase in acoustic signal strength by forming an acoustic echo chamber in which membrane 430 acts as a drumhead and resonant cavity 440 acts as a drum. The resonance of the very low frequency acoustic signals within resonant cavity 440 causes the amplitudes of the acoustic waves within resonant cavity 440 to combine in phase and thereby increase the acoustic signal strength of the acoustic signals that were originally incident on membrane 430.

The increase in amplitude of the signals provided by the interaction of membrane 430 and resonant cavity 440 enables microphone 110 to efficiently detect signals in the very low frequency range of one tenth Hertz (0.1 Hz) to thirty Hertz (30.0 Hz). This very low frequency range includes the very low frequency range used to detect respiration signals (i.e., one tenth Hertz (0.1 Hz) to two Hertz (2.0 Hz)) and the very low frequency range used to detect cardiac information signals (i.e., ten Hertz (10.0 Hz) to thirty Hertz (30.0 Hz)). The interaction of membrane 430 and resonant cavity 440 assists microphone 110 in detecting very low acoustic signals in the required signal ranges.

To improve reception of the very low frequency acoustic signals, the surface area of membrane 430 is larger than the surface area of the face 160 of microphone 110. In an advantageous embodiment of the present invention the surface area of membrane 430 is at least five (5) times greater than the surface area of the face 160 of microphone 110. The presence of membrane 430 significantly increases the area which may be acoustically coupled to microphone 110. The relatively large area of membrane 430 permits larger areas of a body to be analyzed than would otherwise be possible.

When microphone 110 receives low frequency acoustic signals then microphone 110 generates electronic signals indicative of the intensity of the low frequency acoustic signals. As previously described, electronic processing circuits (not shown) in a physiological condition monitor (not shown) are coupled to microphone 110 through microphone output cables, 170 and 180, to receive and analyze the electronic signals that are indicative of the intensity of the low frequency acoustic signals.

Although the present invention has been described in detail, those skilled in the art should understand that they can make various changes, substitutions and alterations herein without departing from the spirit and scope of the invention in its broadest form.

What is claimed is:

1. A sensor capable of detecting very low frequency acoustic signals, said sensor capable of being acoustically coupled to a source of acoustic signals, and said sensor capable of receiving low frequency acoustic signals in the frequency range of one tenth Hertz to nine and nine tenths Hertz and generating electronic signals indicative of the intensity of said low frequency acoustic signals.

2. A sensor as claimed in claim 1 wherein said sensor comprises:
   a chamber capable of being acoustically coupled to a source of acoustic signals, said chamber having portions that define a cavity within said chamber, and
   a microphone capable of receiving low frequency acoustic signals within said cavity of said chamber in the frequency range of one tenth Hertz to nine and nine tenths Hertz and capable of generating electronic signals indicative of the intensity of said low frequency acoustic signals.

3. The sensor as claimed in claim 2 wherein said chamber is a closed chamber filled with a fluid.

4. The sensor as claimed in claim 3 wherein said fluid is air.

5. The sensor as claimed in claim 2 wherein said chamber is an open chamber filled with air.

6. The sensor as claimed in claim 2 wherein said chamber is formed having nonrigid walls.

7. The sensor as claimed in claim 6 wherein said nonrigid walls are capable of moving inwardly and outwardly with respect to the interior of said cavity in response to the presence of low frequency acoustic energy.

8. A sensor capable of detecting very low frequency acoustic signals in the frequency range of one tenth Hertz to thirty Hertz comprising:
   a chamber capable of being acoustically coupled to a source of acoustic signals, said chamber having portions that define a cavity within said chamber, and said chamber having nonrigid walls capable of moving inwardly and outwardly with respect to the interior of said cavity in response to the presence of low frequency acoustic energy; and
   a microphone placed within said cavity of said chamber capable of receiving low frequency acoustic signals within said cavity of said chamber that are caused by the inward and outward motion of said nonrigid walls of said cavity, and capable of generating electronic signals indicative of the intensity of said low frequency acoustic signals.

9. The sensor as claimed in claim 2 further comprising:
   a membrane attached to said chamber covering said cavity of said chamber, said membrane capable of moving in response to very low frequency acoustic signals incident on said membrane to cause said very low frequency acoustic signals to be transmitted through said cavity to said microphone.

10. The sensor as claimed in claim 9 wherein the movements of said membrane amplify the intensity of said very low frequency acoustic signals within said cavity.

11. The sensor as claimed in claim 10 wherein said movements of said membrane amplify the intensity of said very low frequency acoustic signals within said cavity by causing said very low frequency acoustic signals to resonate within said cavity.

12. The sensor as claimed in claim 8 further comprising:
   a membrane attached to said chamber covering said cavity of said chamber, said membrane capable of moving in response to very low frequency acoustic signals incident on said membrane to cause said very low frequency acoustic signals to be transmitted through said cavity to said microphone.

13. The sensor as claimed in claim 12 wherein the movements of said membrane amplify the intensity of very low frequency acoustic signals within said cavity.

14. The sensor as claimed in claim 13 wherein said movements of said membrane amplify the intensity of very low frequency acoustic signals within said cavity by causing very low frequency acoustic signals within said cavity to resonate within said cavity.

15. A method for detecting very low frequency acoustic signals comprising the steps of:
   acoustically coupling a low frequency sensor to a source of low frequency acoustic signals;
   receiving in said low frequency sensor acoustic signals in the range of one tenth Hertz to nine and nine tenths Hertz; and
   generating in said low frequency sensor electronic signals indicative of the intensity of said low frequency acoustic signals.

16. A method for detecting low frequency acoustic signals comprising the steps of:
   forming a chamber having portions that define a cavity within said chamber;
   placing a microphone within said cavity of said chamber;

acoustically coupling said chamber to a source of low frequency acoustic signals;

receiving in said microphone acoustic signals in the range of one tenth Hertz to nine and nine tenths Hertz; and generating in said microphone electronic signals indicative of the intensity of said low frequency acoustic signals.

17. A method as claimed in claim 16 comprising the further steps of:

forming the walls of said chamber with nonrigid material capable of moving inwardly and outwardly with respect to the interior of said cavity in response to the presence of low frequency acoustic energy; and receiving in said microphone acoustic signals in the range of one tenth Hertz to nine and nine tenths Hertz within said cavity of said chamber that are caused by the inward and outward motion of said nonrigid walls of said cavity.

18. A method for detecting low frequency acoustic signals comprising the steps of:

forming a chamber having portions that define a cavity within said chamber;

forming the walls of said chamber with nonrigid material capable of moving inwardly and outwardly with respect to the interior of said cavity in response to the presence of low frequency acoustic energy;

placing a microphone within said cavity of said chamber;

attaching a membrane to said chamber wherein said membrane covers said cavity of said chamber and wherein said membrane is capable of moving in response to very low frequency acoustic signals incident on said membrane;

acoustically coupling said membrane to a source of low frequency acoustic signals;

receiving in said microphone acoustic signals in the range of one tenth Hertz to thirty Hertz within said cavity of said chamber that are caused by the movements of said membrane; and generating in said microphone electronic signals indicative of the intensity of said low frequency acoustic signals.

19. A method as claimed in claim 18 comprising the further steps of:

amplifying said low frequency acoustic signals within said cavity of said chamber; and receiving in said microphone said amplified acoustic signals in the range of one tenth Hertz to thirty Hertz.

* * * * *